United States Patent [19]

Horodysky et al.

[11] Patent Number: 4,617,133

[45] Date of Patent: Oct. 14, 1986

[54] FRICTION REDUCING, ANTIWEAR ADDITIVES

[75] Inventors: Andrew G. Horodysky, Cherry Hill; Henry Ashjian, East Brunswick, both of N.J.

[73] Assignee: Mobil Oil Corporation, New York, N.Y.

[21] Appl. No.: 639,179

[22] Filed: Aug. 9, 1984

[51] Int. Cl.$^4$ .................. C10M 1/44; C10M 3/38; C10M 5/24; C10M 7/24
[52] U.S. Cl. ........................................ 252/32.5; 44/63
[58] Field of Search ................... 252/32.5; 548/119

[56] References Cited

U.S. PATENT DOCUMENTS

| | | | |
|---|---|---|---|
| 3,920,567 | 11/1975 | Miller | 252/32.5 |
| 3,956,305 | 5/1976 | Mudd | 548/119 |
| 4,522,629 | 6/1985 | Horodysky et al. | 44/53 |
| 4,532,057 | 7/1985 | Harodysky et al. | 252/49.8 |

Primary Examiner—Mrs. Y. Harris-Smith
Attorney, Agent, or Firm—Alexander J. McKillop; Michael G. Gilman; Howard M. Flournoy

[57] ABSTRACT

Oxazoline salts of acid phosphates derived from hydrocarbyl diols are effective multifunctional friction reducing additives when incorporated into various fluid hydrocarbyl compositions.

7 Claims, No Drawings

FRICTION REDUCING, ANTIWEAR ADDITIVES

BACKGROUND OF THE INVENTION

This invention is directed to lubricant additives and compositions thereof, and more particularly to liquid hydrocarbyl fuels and lubricant compositions, comprising said fuels or oils of lubricating viscosity or greases prepared therefrom containing friction reducing amounts of oxazoline salts of acid phosphates derived from hydrocarbyl diols.

Phosphorus-containing additives have been extensively used in lubricant applications. These additives include phosphites, phosphate esters, acid phosphates, phosphonates, metallic dithiophosphates and the like.

Imidazolines have found use as friction reducing additives as described in U.S. Pat. Nos. 4,394,278 and 4,298,486. U.S. Pat. No. 4,427,562 discloses imidazolines and certain esters thereof as known antifriction additives. U.S. Pat. No. 4,163,731 is directed to certain fire resistant functional fluids based on phosphate esters and substituted aromatic compounds, as for example, heterocyclic compounds such as oxazolines.

Hydroxyl-containing additives and their derivatives are well-known for their water scavenging properties when formulated into fuels and for their lubricity characteristics when blended into lubricants. The use of glycerol monooleate and similar hydroxyl-containing carboxylates have found wide spread commercial use as lubricant additives. The use of related diols is described in U.S. Pat. Nos. 3,649,358 and 3,899,433.

The hydrocarbyl-diol derived oxazoline salts of acid phosphates as disclosed herein contribute excellent friction reducing properties when formulated at low additive concentrations into hydrocarbyl fuels, fluid lubricants and greases. The modest acid phosphate content provides the basis for significant synergistic wear activity in the highly surface active molecules of the embodied products. The basis for antirust and anticorrosion properties is provided by the nitrogen-containing heterocyclic moiety, particularly the acid phosphates.

To the best of applicants' knowledge and belief, both the additive structures per se and the lubricant compositions containing such additives are novel. Further, the unique compositions disclosed herein are not known to have been previously used as multifunctional friction reducing antiwear or antirust additives in hydrocarbyl lubricating oils, greases, or fuels.

SUMMARY OF THE INVENTION

In accordance with the invention, there is provided additive products comprising various oxazoline salts of diol-derived acid phosphates and a variety of compositions comprising synthetic and mineral oil based lubricants and greases and fuels into which said oxazoline salts have been incorporated.

DESCRIPTION OF SPECIFIC EMBODIMENTS

The novel additive products of this invention are generally prepared in the manner given below.

Long chain hydrocarbyl vicinal diols are (1) converted to their corresponding acid phosphates or partial acid phosphates by reaction with, for example, phosphorus pentoxide and (2) converted to the oxazoline salts of the acid phosphates by reaction with various hydroxyalkyl oxazolines such as:

$R^3(OH)_2$ or more preferred

where $R = C_3-C_{30}$ hydrocarbyl, and $R^1 =$ hydrogen or $C_1-C_6$ hydrocarbyl and $R^3 = C_8-C_{32}$ hydrocarbyl.

Any suitable oxazoline may be used herein. Preferred oxazolines are hydroxyalkyl oxazolines such as, for example

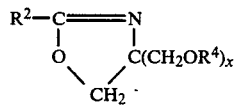

where $R^2$ is alkyl, alkenyl, cycloalkyl, cycloalkenyl, aryl, alkaryl, aralkyl of from about 5 to about 29 carbon atoms, $R^4$ is hydrogen or $C_1-C_{18}$ acyl, when $x=2$, one $R^4$ may be hydrogen and one $R^4$ may be acyl or both may be the same, and x is from 1 to 2. Oxazoline esters and oxazoline diesters can also be used as in the case where an organic acid such as 2 or 3 moles of oleic acid is reacted with one mole of tris(hydromethyl)aminomethane. The $R^2$—C— grouping can be derived from oleyl, linoleyl, coco, stearyl, isostearyl, hydrogenated tallow, dodecyl or similar moieties or mixtures of similar groups. The described oxazolines may be readily obtained commercially or prepared in any convenient manner known to the art.

Preferred diols include 1,2-dodecanediol, 1,2-tetradecanediol, 1,2-pentadecanediol, 1,2-hexadecanediol, 1,2-heptadecanediol, 1,2-octadecanediol, mixtures of such diols and diols prepared by the hydrolysis of epoxides of propylene trimer, propylene tetramer, butylene trimers and tetramers and similar diols.

The diol or polyol is converted to at least the partial acid phosphate by reaction with 5–100% molar quantities, and preferably 25–75% molar quantities of phosphorus pentoxide followed by at least partial conversion to the oxazoline salts by reaction with the appropriate heterocyclic compound.

The diol, polyol or mixtures thereof are reacted with phosphorus pentoxide under ambient conditions or at temperatures of from about 50° to 150° C. Higher pressures may be used if desired. Conversion to the oxazoline salt is accomplished under essentially the same reaction conditions with 25–150% molar quantities.

In general, in most instances, the product is employed in an amount from about 0.1% to about 10% by weight, and preferably in an amount of from about 0.5% to about 5% by weight of the total weight of the composition. When used in fuels, the product may be present from about 0.00001 to about 1% by weight, preferably from about 0.001 to about 0.01% by weight. Of particular significance, is the ability of the additive products in such minor amounts to counteract the accelerating effect of oxidation on metal and on lubricant deterioration.

These products may be incorporated into either mineral or synthetic oils or mixtures thereof, or greases in which any of the aforementioned oils are employed as a vehicle. These compositions can also contain detergents and dispersants, as well as inhibitors, antiwear, extreme pressure, antifoam, pour depressant, and viscosity index improving additives or other additives of their known purposes without negating the beneficial properties of the novel compositions of this invention.

In general, mineral oils employed as the lubricant or grease vehicle may be of any suitable lubricating vicosity range, as for example, from about 45 SSU at 100° F. to about 6,000 SSU at 100° F., and preferably from about 50 SSU at 210° F. to about 250° SSU at 210° F. These oils may have viscosity indexes varying from below 0 to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease of formulation.

In instances where a synthetic oil or synthetic oils are employed as the vehicle for the grease, in preference to mineral oils, or in combination therewith, various components may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl) adipate, di(-butylphthalate) fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis (p-phenoxy phenyl) ether, phenoxy phenylethers, etc.

Greases in accordance with the present invention containing the above-described products, are prepared by combining an oil of lubricating viscosity with a grease-forming quantity of a thickening agent. For this purpose, a wide variety of materials may be employed. The thickening or gelling agents may include any of the conventional metal salts or soaps, which are dispersed in the lubricating vehicle in grease-forming quantities, in such degree as to impart to the resulting grease composition the desired consistency. Other thickening agents that may be employed in the grease formation may comprise the non-soap thickeners, such as surface modified clays and silicas, aryl ureas, calcium complexes and similar materials. In general, grease thickeners may be employed which do not melt and dissolve when used at the required temperature within a particular environment, however, in all other respects, any materials which are normally employed for thickening or gelling hydrocarbon fluids for forming grease, can be used in preparing the greases in accordance with the present invention.

Although the following examples specifically illustrate the invention, it is understood that they are meant to be illustrations and not limitations to the invention.

EXAMPLE 1

Hydrocarbyl Dihydroxymethyl Oxazoline

Approximately 1400 g of oleic acid, 70 g isostearic acid, 500 g xylene and 635 g trishydroxymethyl aminomethane were charged to a 5 liter glass reactor equipped with heater, agitator, Dean-Stark tube with condenser and provision for blanketing vapor space with nitrogen. The reactor contents were heated to 180° C. over a period of about 10 hours until no more water was collected, to form the oxazoline. A total of approximately 200 g water was collected.

EXAMPLE 2

Partial Acid Phosphate of 1,2-Mixed-Pentadecanediol-Octadecanediol

Approximately 480 g of 1,2-mixed-pentadecanediol-octadecanediol (obtained commercially as Vikol 158 from Viking Chemical Company, and containing approximately 28% 1,2-pentadecanediol, 28% 1,2-hexadecanediol, 28% 1,2-heptadecanediol and 16% 1,2-octadecanediol) and 200 g hexane were charged to a 2 liter reactor equipped with heater agitator and Dean-Stark tube with condenser. The contents were warmed to about 60° C. and 70 g phosphorus pentoxide were slowly added over a period of two hours while maintaining a temperaure of about 60°–70° C. The temperature was raised to 100° C. for three additional hours. After removing some of the solvent, the remaining solvent was completely removed by distillation under reduced pressure at about 100° C.

EXAMPLE 3

Acid Phosphate of Mixed 1,2-Pentadecanediol-1,2-Octadecanediol

Approximately 480 g of mixed 1,2-pentadecanediol-1,2-octadecanediol (obtained commercially as Vikol 158 from Viking Chemical Co. and containing approximately 28% 1,2-pentadecanediol, 28% 1,2-hexadecanediol, 28% 1,2-heptadecanediol and 16% 1,2-octadecanediol) and 200 g hexane were charged to a 2 liter reactor equipped with heater, agitator and Dean Stark tube with condenser and heated to approximately 60° C. Over a period of about 2 hours, 70 g of phosphorus pentoxide was added. The temperature was raised to 100° C. for an additional 3 hours after removing some solvent by distillation. The solvent was completely removed by vacuum distillation of about 100° C. resulting in a clear, straw yellow liquid.

EXAMPLE 4

Hydrocarbyl Dihydroxymethyl Oxazoline Salt of Acid Phosphate of Mixed 1,2-Pentadecanediol-1,2-Octadecanediol Approximately 55 g of the acid phosphate of Example 3 was placed into a glass reactor equipped with agitator and warmed to approximately 60°–65° C. Approximately 35 g of the oxazoline of Example 1 was added in 3 portions over a period of ½ hour and held at about 60°–65° C. a period of two hours. This temperature was maintained at about 60°–65° C. for an additional one hour with agitation. The product was an odorless clean yellow-orange fluid which formed a pale amber waxy solid upon cooling.

EXAMPLE 5

Hydrocarbyl Dihydroxymethyl Oxazoline Salt of Acid Phosphate of Mixed 1,2-Pentadecanediol-1,2-Octadecanediol Approximately 55 g of the acid phosphate of Example 3 was placed in a glass reactor equipped with agitator and warmed to about 60°–65° C. Approximately 50 g of the oxazoline of Example 1 was added in 3 portions over a period of ½ hour and held at about 60°–65° C. for an additional 1 hour with agitation. The product was an odorless, clear yellow-orange fluid which formed a pale amber waxy solid upon cooling.

The use of only 1% of the product of Example 4 reduced the coefficient of friction by 36% as shown in Table 1. These additives are accordingly effective friction reducers.

EVALUATION OF PRODUCTS

Low Velocity Friction Apparatus

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of the X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed.

Freshly polished steel specimens are used for each run. The surface of the steel is parallel ground to 4-8 microinches.

The data obtained are shown in Tables 1 and 2. The percentages by weight are percentages by weight of the total lubricating oil composition, including the usual additive package. The data are percent decrease in friction according to:

$$\frac{(U_k \text{ of oil alone}) - (U_k \text{ of additive plus oil})}{(U_k \text{ of oil alone})} \times 100$$

The value for the oil alone would be zero for the form of the data shown in the Tables.

TABLE 1

Friction Test Results Using Low Velocity Friction Apparatus

| | Additive Conc. in Test Oil Weight % | % Reduction in Coefficient of Friction at 5 Ft/Min | % Reduction in Coefficient of Friction at 30 Ft/Min |
|---|---|---|---|
| Base Fluid A (fully formulated synthetic engine oil containing detergent/dispersant/inhibitor performance package) SAE 5W 30 | — | 0 | 0 |
| Example 4 | 2 | 41 | 42 |
| Hydrocarbyl dihydroxymethyl oxazoline salt of partial acid phosphate of mixed 1,2-pentadecanediol-1,2-octadenanediol | 1 | 36 | 26 |
| Example 5 | 2 | 46 | 39 |
| Hydrocarbyl dihydroxymethyl oxazoline salt of partial acid phosphate of mixed 1,2-pentadecanediol-1,2-octadenanediol | 1 | 36 | 20 |

The above data clearly demonstrate that the use of oxazoline derivatives of acid phosphates in premium quality automotive and industrial lubricants significantly enhances the lubricants friction modifying characteristics.

Example 4 was also tested for antiwear properties. In order to demonstrate the improvement in antiwear properties realized by employing the above-described novel compositions, compared with that present in the untreated organic composition, comparative data were obtained in accordance with a modified Four-Ball Wear Test. The standard test is described in U.S. Pat. No. 3,423,316. In general, in the test, three steel balls of 62-100 steel are held in a ball cup. A fourth ball positioned on a rotatable vertical axis is brought into contact with the three balls and is rotated against them. The force which the fourth ball is held against the three stationary balls may be varied according to a desired load. The test lubricant is added to the ball cup and acts as a lubricant for the rotation. In the modified test the force is 60 kg, at 1500 rpm's at temperature of 175° and 275° F. At the end of the test, the steel balls are investigated for wear-scar, the extent of scarring represents the effectiveness of the lubricant as an antiwear agent. The oil employed in accordance with the test results shown in the following Table 2 comprised a solvent-refined mineral lubricating oil. In the data of the table, the additive was employed in concentration of 1% by weight. The resultant data is set forth in Table 2.

TABLE 2

Modified 4-Ball Wear Test

| | 80% Solvent Paraffinic Bright, 20% 300 Second Solvent Paraffinic Neutral Lubricating Oil/ | 1% Example 4 in 80% Solvent Paraffinic Bright, 20% 300 Second Solvent Paraffinic Neutral Lubricating Oil |
|---|---|---|
| Test Conditions 175° F., 60 Kg Load, 30 minutes 1500 RPOM | | |
| Scar Diameter, Avg Final, mm | 1.98 | 0.51 |
| Test Conditions 275° F., 60 Kg Load, 30 Minutes | | |

TABLE 2-continued

| Modified 4-Ball Wear Test | |
|---|---|
| 80% Solvent Paraffinic Bright, 20% 300 Second Solvent Paraffinic Neutral Lubricating Oil/ | 1% Example 4 in 80% Solvent Paraffinic Bright, 20% 300 Second Solvent Paraffinic Neutral Lubricating Oil |
| 1500 RPM | |
| Scar Diameter, Avg Final, mm | 2.23 | 0.50 |

As can be seen, the oxazoline salts of the acid phosphates possess excellent antiwear properties as measured in the 4-Ball Machine under the above extreme temperature, load and speed conditions. The novel compositions described herein are effective at low concentrations are non-metallic and do not contain any potentially corrosive sulfur and provide an unexpected combination of friction reduction and antiwear activity.

It is understood by those of ordinary skill in the art that departure from the preferred embodiments described herein can be effectively made and that such departures are within the scope of the specification.

We claim:

1. A lubricant composition comprising a major amount of an oil of lubricating viscosity of grease prepared therefrom and a minor amount of an additive compound effective for providing multifunctional friction reducing and antiwear properties to said composition consisting essentially of an oxazoline salt of a vicinal diol derived acid phosphate wherein said oxazoline salt is derived from an oxazoline having the following generalized structure

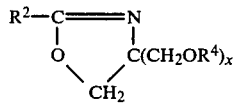

where $R^2$ is alkyl alkenyl, cycloalkyl, cycloalkenyl, aryl, alkaryl or aralkyl of from about 5 to about 29 carbon atoms and x is from 1 or 2, $R^4$ is hydrogen or acyl and when x is 2 one $R^4$ may be hydrogen and one $R^4$ may be acyl or both may be hydrogen or acyl.

2. The composition of claim 1 wherein the additive compound, described therein is the hydrocarbyl dihydroxymethyl oxazoline salt of the acid phosphate of mixed 1-2-pentadecanediol and 1-2-octadecanediol.

3. The composition of claim 1 wherein said oil is a mineral or synthetic oil or mixtures thereof.

4. The composition of claim 1 wherein said major proportion is a grease.

5. A method or reducing fuel consumption in internal combustion engines comprising treating the moving surfaces thereof with a lubricant composition as described in claim 1.

6. A product of reaction prepared by reacting an ozazoline and the acid phosphate of a vicinal diol whereby the oxazoline salt of the acid phosphate or partial acid phosphate of the vicinal diol is prepared and wherein said oxazoline is represented by the general formula

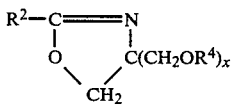

where $R^2$ is alkyl, alkenyl, cycloalkyl, cycloalkenyl, aryl, alkaryl or aralkyl of from about 5 to about 29 carbon atoms and x is from 1 to 2, $R^4$ is hydrogen or acyl and when x is 2 one R—$^4$ may be hydrogen and one R—$^4$ may be acyl or both may be the same.

7. A product of reaction prepared as in claim 6 wherein the compound is hydrocarbyl dihydroxymethyl oxazoline salts of the acid phosphate of mixed 1-2-pentadecanediol and 1-2-octadecanediol.

* * * * *